United States Patent [19]

Moore

[11] Patent Number: Plant 5,977

[45] Date of Patent: May 12, 1987

[54] ROSE PLANT/VAR: MORCHEER

[76] Inventor: Ralph S. Moore, 2519 E. Noble Ave., Visalia, Calif. 93277

[21] Appl. No.: 781,692

[22] Filed: Sep. 30, 1985

[51] Int. Cl.[4] ..... A01H 5/00

[52] U.S. Cl. ..... Plt./10

[58] Field of Search ..... Plt./10

*Primary Examiner*—Robert E. Bagwill

[57] ABSTRACT

This invention relates to a new and distinct variety of miniature rose plant primarily identified by small very full double medium red flowers of excellent lasting quality.

1 Drawing Figure

1

The present invention relates to a new and distinct variety of hardy, dwarf, bush type rose plant of the miniature class; the variety being primarily characterized—as to novelty—by the very full (double) flowers of medium red color which are similar to My Valentine (miniature—U.S. Plant Pat. No. 3,935).

The variety is further characterized by:

An abundance of bloom, with flowers usually borne several to the stem in small clusters and sometimes singly.

Little or no fragrance.

A plant which is vigorous, of rounded, upright shape with small semi-glossy to matt foliage with pointed leaflets; the buds and flowers being similar in form to My Valentine (miniature—U.S. Plant Pat. No. 3,935) but slightly larger and of a brighter red color.

The plant, which has a normal mature height of 12–14 inches (taller in greenhouse) can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at Sequoia Nursery located at Visalia, Calif., under conditions of careful control and observation, as a cross between Fairy Moss (U.S. Plant Pat. No. 3,083) as the seed parent and Orange Honey (U.S. Plant Pat. No. 4,496) as the pollen parent.

Subsequent to origination of the variety I successfully asexually reproduced it at Sequoia Nursery, located as aforesaid, by budding as well as by cuttings; the reproductions having run true in all respects.

The color photograph illustrates the variety, including the foliage, and flowers.

Referring now specifically to the new and distinct variety of miniature rose plant, the following is a detailed description thereof in outline; all major color plate identifications being by reference to The British Colour Council Horticultural Colour Chart, except where common terms of color definition are employed.

Type: Hardy; dwarf; bushy; upright; seedling; greenhouse; outdoors; cut flowers; garden decoration; potted plant.

Class: Miniature. Variety identification: Morcheer—(-Commercial Synonym: Cheerleader).

Flowers borne: Singly and several together (3 to 5) on slender wirey stems.

2

Quantity of bloom: Abundant both outside and in greenhouse.

Bud:

*Peduncle.*—Medium length; slender but sturdy; erect; medium green, sometimes tinted bronze (outdoors); with numerous short hairs.

*Before calyx breaks; size.*—Small. Form medium long, ovoid to pointed, with several small foliaceous apendages and numerous short hairs on surface of bud; with foliaceous parts extending beyond the tip of the bud equal to one-half or more of its length.

*Color.*—Medium green, occasionally tinted with bronze (outdoors).

*As calyx breaks, color.*—Red.

*Opening.*—Opens well in all weather.

Bloom:

*Size when fully open.*—Small, averaging about 30 mm ($1\frac{1}{4}''$).

*Petalage.*—Double — averaging about 60 petals, arranged regularly plus several petaloids.

*Form.*—Cupped at first and becoming full with reflexed petals (resembles a small Chrysanthemum). Open flowers show no stamens.

Petals: fairly thick; velvety on inside surface and satiny on outside surface.

*Shape.*—Outside petals, broad lanceolate (nearly round) with rounded or very short acute tip; intermediate — broad lanceolate with very short acute tip; inside — lanceolate with acute tip.

Color: Newly opened flower from a plant grown outdoors; (September 1985), Visalia, Calif.

*Outside petal.*—Outside surface — white at base blending into red (near Chrysanthemum Crimson 824/3) on tip 2/3, the red color being streaked with white (color is basically white with the red bleeding through from upper surface). Inside surface — brighter red, near Cardinal Red 822/1 or 822/2 with white on basal $\frac{1}{4}$ of petal. Red color may be a bit lighter than above or modified with blackish shading (difficult to capture in color photos).

*Intermediate petal.*—Outside surface — similar to outside petal. Inside surface — similar to outside petal.

*Inner petal.*—Outside surface — similar to intermediate petal; inside surface — similar to intermediate petal. General color effect; newly opened flower — color — bright red. Three days open color — similar to fresh open flowers, but less bright. Behavior — opens well in all weather. Spent petals or flower drop off. Flower longevity (July–August 1985) — plant in pot 6–10 days or longer. Cut flowers at living room temperature — 5 to 7 days or longer.

Reproductive organs:

*Stamens.*—Few.

*Filaments.*—Varying length.

*Anthers.*—Yellow.

*Pollen.*—Little or none.

*Pistils.*—Average number.

*Styles.*—Varying length; greenish; bunched.

*Ovaries.*—All enclosed in calyx.

*Hips.*—None.

*Sepals.*—Permanent; spear shaped; recurved.

*Seed.*—None.

Foliage:

*Leaves.*—Compound of five (sometimes three or seven) leaflets; small; leathery; semi-glossy to matt.

*Leaflets.*—Shape: broad lanceolate; apex acute; base — rounded.

*Color.*—Medium green; new growth — normal (medium) green (sometimes tinted reddish).

*Rachis.*—Medium strength; upper side usually smooth (may have a few very short hairs); grooved; underside may have several small thorns (or claws) and few to no short prickles.

*Stipules.*—Medium length; medium to narrow width; medium to short length narrow points which turn out usually at about 45 degrees or less.

Growth:

*Habit.*—Dwarf; bushy; upright; much branched.

*Growth.*—Vigorous; internodes short.

*Canes.*—Medium; slender; sturdy.

*Main stems.*—Color: medium green.

*Thorns.*—Several — of varying size and length — generally straight, inclined slightly downward; color — grey.

*Hairs.*—Few or none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, upright, much branched habit, substantially as illustrated and described, characterized by buds and flowers of medium red coloring, the bud and flower resembling in form My Valentine (miniature—U.S. Plant Pat. No. 3,935) but slightly larger size and brighter color, with full open flower being rounded and similar in form to a button Chrysanthemum; and further characterized by a plant of compact, vigorous, well rounded shape, with main stems and shoots of average thorniness, the said plant being easy to propagate from soft wood cuttings, with an abundance of small semi-glossy to matt foliage, the flowers being borne singly or several to the stem in clusters.

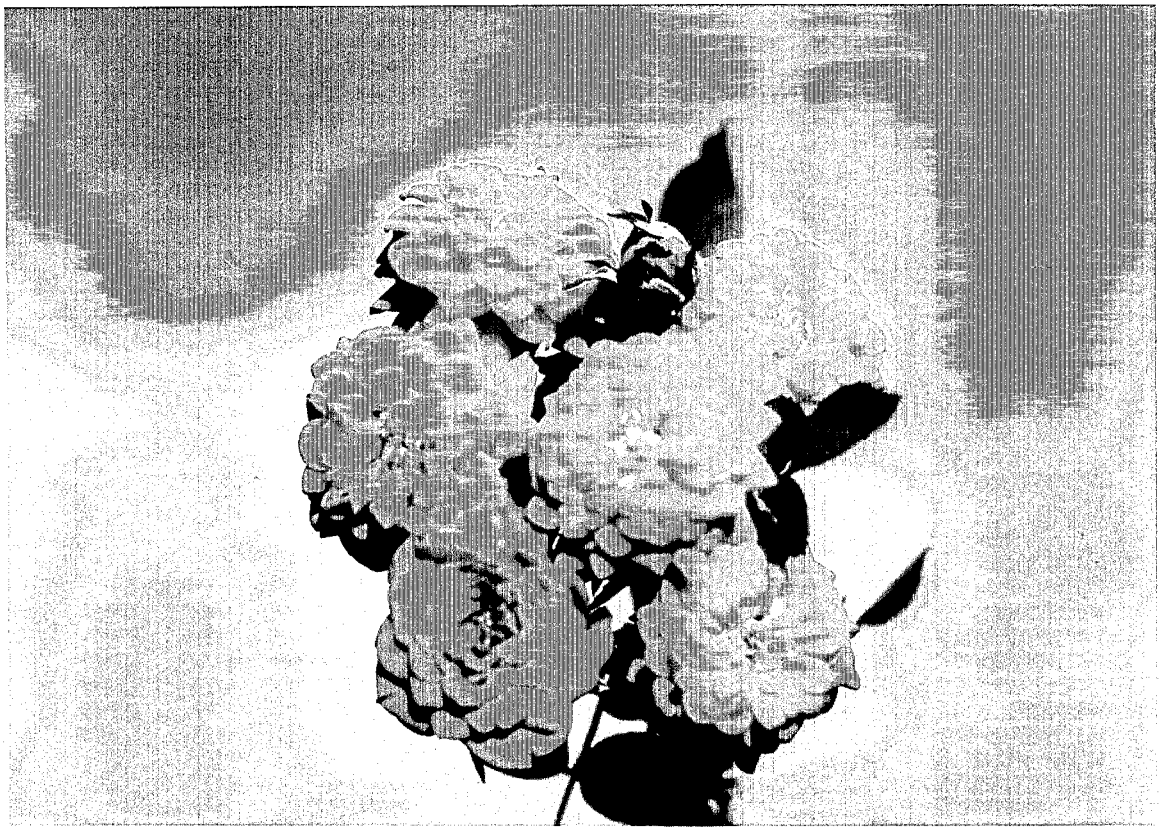

* * * * *